(12) United States Patent
Lagercrantz et al.

(10) Patent No.: US 8,224,421 B2
(45) Date of Patent: Jul. 17, 2012

(54) IMPLANTABLE CARDIAC STIMULATOR, DEVICE AND SYSTEM FOR MONITORING THE STATUS OF A CARDIAC LEAD

(75) Inventors: Per Lagercrantz, Stockholm (SE); Anna-Karin Johansson, Vallentuna (SE); Karin Järeverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 707 days.

(21) Appl. No.: 12/160,970

(22) PCT Filed: Jan. 31, 2006

(86) PCT No.: PCT/SE2006/000142
§ 371 (c)(1),
(2), (4) Date: May 11, 2009

(87) PCT Pub. No.: WO2007/089175
PCT Pub. Date: Aug. 9, 2007

(65) Prior Publication Data
US 2009/0306735 A1    Dec. 10, 2009

(51) Int. Cl.
*A61B 5/01* (2006.01)
*A61B 5/05* (2006.01)

(52) U.S. Cl. ........ 600/412; 600/474; 600/549; 600/555; 607/21; 607/119

(58) Field of Classification Search ............... 600/412, 600/474, 549, 555; 607/21
See application file for complete search history.

(56) References Cited

U.S. PATENT DOCUMENTS

| | | | |
|---|---|---|---|
| 5,336,244 A | | 8/1994 | Weijand |
| 5,520,190 A | | 5/1996 | Benedict et al. |
| 5,596,995 A | * | 1/1997 | Sherman et al. ............. 600/549 |
| 5,938,694 A | * | 8/1999 | Jaraczewski et al. ......... 607/122 |
| 5,989,192 A | | 11/1999 | Weijand et al. |
| 6,063,078 A | * | 5/2000 | Wittkampf ....................... 606/41 |
| 6,571,130 B1 | | 5/2003 | Ljungström et al. |
| 2002/0028999 A1 | | 3/2002 | Schaldach et al. |
| 2002/0103429 A1 | * | 8/2002 | deCharms ..................... 600/410 |
| 2009/0306638 A1 | * | 12/2009 | Hillely et al. ................... 606/21 |

FOREIGN PATENT DOCUMENTS

| | | |
|---|---|---|
| WO | WO 99/53972 | 10/1999 |
| WO | WO 2006/135293 | 12/2006 |

\* cited by examiner

*Primary Examiner* — Carl H Layno
*Assistant Examiner* — Natasha Patel

(57) ABSTRACT

A cardiac stimulator has an implantable cardiac lead that carries a temperature sensitive element with a surface thereof in contact with biological matter. The temperature sensitive element emits a temperature signal corresponding to the temperature of biological matter, such as blood, in contact with the surface of the temperature sensitive element. Processing circuitry receives the temperature signal and determines a variability thereof within a selected time interval. A status signal is emitted dependent on this variability.

23 Claims, 4 Drawing Sheets

IMPLANTABLE CARDIAC STIMULATOR, DEVICE AND SYSTEM FOR MONITORING THE STATUS OF A CARDIAC LEAD

BACKGROUND OF THE INVENTION

1. Field of the Invention

The present invention generally relates to the field of implantable heart stimulation devices, such as pacemakers, implantable cardioverter-defibrillators (ICD), and similar cardiac stimulation devices. More specifically, the present invention relates to a device for monitoring the status of a cardiac lead implanted in a human heart, a cardiac stimulator comprising such a device, a system comprising such cardiac stimulator and implantable lead, and a method for monitoring the status of a cardiac lead.

2. Description of the Prior Art

Implantable heart stimulators that provide stimulation pulses to selected locations in the heart have been developed for the treatment of cardiac diseases and dysfunctions. Generally, the stimulation pulses are delivered via implantable leads comprising stimulation electrodes for intracardiac delivery of electrical pulses. Furthermore, sensors may be provided within the heart, such as intracardiac sensors for sensing electrical activities and events within the heart, blood pressure, acceleration, and/or other physiological parameters. Such parameters may be used for adapting the energy content of the stimulation pulses for ensuring cardiac capture while avoiding unnecessary energy consumption, adapting the cardiac rate and cardiac output to the varying need of the patient, i.e. rate adaptation, etc.

The implanted position for the respective intracardiac electrode or sensor is dependent on its purpose. For instance, an intracardiac electrode arranged at the distal end of a cardiac lead for delivering stimulation pulses is generally implanted to be in contact with myocardial tissue. Following implantation, an ingrowth of the distal end containing the electrode into the myocardial tissue preferably occurs. A dislocation of the cardiac lead from the myocardial tissue may lead to a severe increase in the energy content of the stimulation pulses in order to effectuate capture, which of course will have a negative effect of the battery life of the cardiac stimulator. On the other hand, a sensor for sensing the intracardiac blood pressure is preferably located in the blood stream and not intended for ingrowth into myocardial tissue.

Another issue related to intracardiac electrodes, in particular for sensing electrodes intended to be placed in the intracardiac blood stream, is that tissue overgrowths, such as protein layers and clots of blood adhering to the sensing surface, may impair the sensing ability of the electrode.

Thus, for many intracardiac electrodes and sensors, the position thereof within the heart is important and there is a need for monitoring or detecting position changes that would effect the function of the electrode, cardiac lead and/or stimulator. Furthermore, a need also exists for monitoring possible overgrowth of intracardiac electrodes and sensors placed in the blood stream of a human heart.

SUMMARY OF THE INVENTION

Thus, an object of the present invention is to address the above-mentioned needs.

According to one aspect of the present invention, a device for monitoring the status of a cardiac lead implanted in a human heart, the device being connectable to a temperature sensitive element in the implantable lead, which temperature sensitive element is sensitive to the temperature of biological matter in contact with the surface of said temperature sensitive element. The device further has processing circuitry configured for receiving a temperature signal from the temperature sensitive element, the temperature signal being indicative of the temperature of the biological matter, determining temperature changes during a selected time interval on the basis of the temperature signal, and providing a status signal indicative of the status of the implantable lead on the basis of temperature changes.

According to a second aspect of the invention, an implantable cardiac stimulator for delivering stimulation pulses to a human heart has a pulse generator enclosed in said housing for generating said stimulation pulses, and control circuitry for controlling the delivery of said stimulation pulses to the heart. The stimulator is connectable to a cardiac lead arrangement for conducting said stimulation pulses to the heart, and for conducting electrical signals from the heart to the control circuitry. The lead arrangement is an implantable lead arranged with a temperature sensitive element that is sensitive to the temperature of biological matter in contact with the surface of said temperature sensitive element. The stimulator also has a device for monitoring the status of the cardiac lead implanted in a human heart, which is connectable to a temperature sensitive element in the implantable lead. The temperature sensitive element is sensitive to the temperature of biological matter in contact with the surface of the temperature sensitive element. The device further has processing circuitry configured for receiving a temperature signal from the temperature sensitive element, the temperature signal being indicative of the temperature of the biological matter, determining temperature changes during a selected time interval on the basis of the temperature signal, and providing a status signal indicative of the status of the implantable lead on the basis of temperature changes.

According to a third aspect of the invention, a cardiac therapy system for delivering stimulation pulses to a human heart has an implantable cardiac stimulator as described in the preceding paragraph, and a cardiac lead arrangement for conducting said stimulation pulses to the heart, and for conducting electrical signals from the heart to the control circuitry. The lead arrangement is an implantable lead arranged with a temperature sensitive element that is sensitive to the temperature of biological matter in contact with the surface of said temperature sensitive element.

According to a fourth aspect of the present invention, a method for monitoring the status of a cardiac lead implanted in a human heart, wherein the implantable lead carries a temperature sensitive element includes the steps of receiving a temperature signal from the temperature sensitive element, the temperature signal being indicative of the temperature of biological matter in contact with the surface of the temperature sensitive element, determining a temperature signal variability in the temperature signal within a selected time interval, wherein the signal variability being indicative of the temperature variability of the biological matter within the selected time interval, and providing a status signal indicative of the status of the implantable lead on the basis of the determined temperature signal variability.

Studies have shown that the temperature of intracardiac blood varies within a respiratory cycle, i.e. a single breath, and even within a single heart beat cycle. One possible reason is that inhaled air generally has a temperature below body temperature. In indoor environments, the difference between ambient air temperature and body temperature, in particular blood temperature, is typically more than 10° C. Through the diffusion of oxygen from the somewhat cooler air to the somewhat warmer blood in the alveoli, a slight decrease in the temperature of the blood is provided through the respiratory cycle. Then, the air in the lungs becomes slowly warmer through heat exchange with the thorax, and the temperature differences between the blood and the inhaled air decreases slowly until the next inhalation.

Furthermore, cooler blood is transported to the slightly warmer heart, and a slight warming of the blood is provided during a single heart beat cycle. This slight temperature variation or change is generally present throughout the respiratory cycle, and can be measured using a suitable temperature sensitive element. Studies have shown intracardiac blood temperature variations of about 0.03-0.05° C. within a respiratory cycle, and of about 0.01.-0.02° C. within a heart beat cycle.

Thus, the present invention is based on the insight of monitoring the status of a cardiac lead implanted in a human heart by monitoring the output signal of a temperature sensitive element subjected to the periodical temperature variations occurring in the blood stream of a human heart, in particular intraventricularly.

It should be noted that for the purposes of the present invention, the slight blood temperature variations occurring within at least a portion of a heart beat cycle or the somewhat larger temperature variations occurring within at least a portion of a respiratory cycle can be used for monitoring the status of an implantable lead. Preferably, the variations occurring within a full heart beat or respiratory cycle is used.

By detecting changes in the output signal from the temperature sensitive element, it can be monitored whether the element is subjected to temperature changes at a level below or above what is expected. As an example, a temperature sensitive element that is intended, after implantation, to be located in the blood stream of a human heart is subjected to the full temperature changes of the blood. This may be reflected in the output signal, or temperature signal, of the temperature sensitive element, which output signal may then be interpreted or converted into a detected temperature change.

If the morphology or amplitude of the output signal changes, and the change is indicative of a decrease in the temperature variations, this can according to exemplifying embodiments be an indication that the sensor element has been brought out of position, for instance have come into contact with an adhered to an intracardiac wall. Thereby, at least a portion of the temperature sensitive element would no longer be in direct contact with blood, but with myocardial tissue which does not fluctuate in temperature as much as the blood during a heart beat or respiratory cycle.

According to further embodiments, the detected decrease in the temperature variations is an indication that the temperature sensitive element is subjected to undesired overgrowth, clotting or protein adherence which reduces the sensing ability of the sensor element. In some embodiments, the output signal of the temperature sensitive embodiment indicating a decrease in temperature variations may be quantitatively analyzed in order to monitor or evaluate the degree or extent of overgrowth to the sensor element. It should be noted that the changes in the output signal may be related to either or both of the morphology and the magnitude of the output signal. For instance, overgrowth on the surface of the temperature sensitive element may result in an offset of the output signal variation, as well as a decrease in the variation amplitudes.

According to further embodiments, if the change is indicative of an increase in the temperature variations, this can also be an indication that the sensor element has been brought out of position. Consider for instance a situation where the temperature sensitive element is arranged at the distal end of the implantable lead near a stimulating electrode, e.g. a tip electrode, and the distal end is arranged to be ingrown or embedded into the myocardial tissue after implantation. Then, a signal output indicating a rise in the temperature variations to which the element is subjected could indicate that the distal end of the implantable lead have become dislocated from the myocardial tissue. As stated above, such a dislocation of the implantable lead, or the stimulating electrode thereof, could result in a severe increase in the energy content of the stimulation pulses in order to effectuate capture.

According to particular embodiments, a sudden and significant change of the output or temperature signal from the temperature sensitive element related to a rise in the temperature variations subjected to the surface of the temperature sensitive element, indicates a sudden dislocation of the implantable lead, or at least of the portion of the implantable lead at which the temperature sensitive element is situated. Preferably, the sudden change and significant change triggers an alarm to the patient for prompting the patient to seek medical assistance for care or follow-up, or directly to the medical care provider, for indicating the possibility that a dislocation of the implantable lead has occurred. Thereby, the medical care provider may determine whether an actual dislocation has occurred and take appropriate corrective action.

According to exemplifying embodiments, the output signal of the temperature sensitive element could be used for detecting micro-dislocations of the implantable lead. Such micro-dislocations are dislocations which may have an effect on the energy requirements for effectuating capture, but which are or may be too small to be detectable through intracorporeal imaging.

According to further embodiments, the device according to the invention may be used for monitoring the successive ingrowth of a temperature sensitive element, and the portion of an implantable lead at which the element is located, following implantation. Then, measurements may be performed at selected time intervals, e.g. once a week, once a month, etc., for determining that the desired ingrowth of the implanted lead progresses as intended.

Furthermore, threshold values may in some embodiments be used for comparison with the obtained sensor output signal, or temperature related signal. The threshold values could for instance be adapted to indicate the dislocation of an implantable lead, or the occurrence of sufficient ingrowth into the myocardium.

In further embodiments, the threshold values could be used for triggering an alarm signal to the patient for prompting the patient to seek medical assistance for care or follow-up, or directly to the medical care provider for indication and subsequent determination of a change in the status of the implantable lead.

According to further embodiments, the temperature sensitive element is made from a piezoelectric material and is arranged for self-cleaning the surface thereof from tissue overgrowth and protein adherence. The self-cleaning is achieved by applying an AC voltage to the temperature sensitive element, which causes the piezoelectric temperature sensitive element to vibrate. This has surprisingly proven to have an efficient cleaning effect on the surface of the sensing element. This effect is further elucidated in the International Application No. PCT/SE2005/00945 (published as WO 2006/135293 A1), the content of which are incorporated herein by reference.

As an example of a suitable temperature sensitive element for use in the present invention, reference is made to the piezoelectric sensor element as described in the International Publication No. WO 99/53972, the contents of which are incorporated herein by reference.

Further objects and advantages of the present invention will be discussed below by means of exemplifying embodiments.

DESCRIPTION OF THE PREFERRED EMBODIMENTS

The following is a description of exemplifying embodiments in accordance with the present invention. This description is intended for describing the general principles and specific embodiments of the invention and is not limited thereto.

Figure 1:
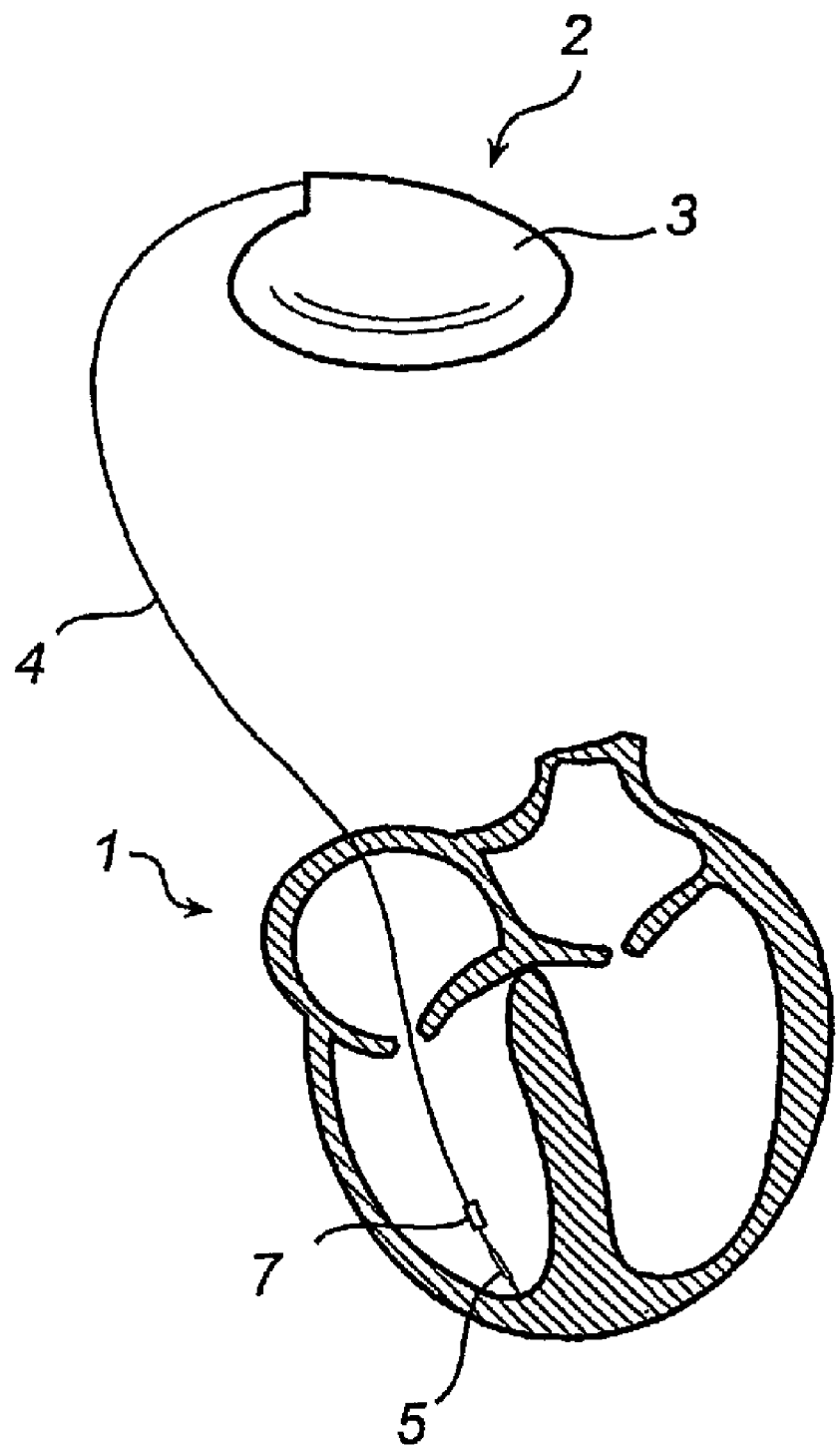
FIG. 1 is a simplified schematic illustration of a medical implant in electrical communication via an implantable lead with a human heart.

Referring first to FIG. 1, there is shown an implantable heart stimulator 2 in electrical communication with a human heart 1 via a cardiac lead 4 arranged for stimulation and sensing. Moreover, the heart stimulator 2 comprises electronic circuitry and a battery contained within a hermetically sealed pacemaker housing 3. The housing 3 comprises a metallic casing of titanium, enclosing the electronic circuitry and battery, and a molded plastic header portion, comprising connector blocks and apertures for receiving the connectors at the proximal ends of the cardiac leads.

The electronic circuitry includes at least one pulse generator for generating stimulation pulses, sensing circuitry for receiving cardiac signals sensed by the cardiac lead 20, and a controller. The controller controls both the sensing of cardiac signals and the delivery of stimulation pulses, for instance as to the duration, energy content and timing of the stimulation pulses.

The stimulation pulses generated by the pulse generator are transmitted via the cardiac lead 4 and delivered to the cardiac tissue by the use of tip electrodes positioned at the distal end 5 of the cardiac lead. Generally, the tip electrode acts as the cathode when the cardiac pulse is delivered. Furthermore, in unipolar cardiac systems, the casing 3 acts as the anode, while in bipolar cardiac systems, the anode is provided by an annular or ring electrode 7 arranged on the cardiac lead at a small distance from the tip electrode.

It should be noted that even though a ring electrode 7 is illustrated in the simplified drawing of FIG. 1, the present invention is equally applicable to unipolar, bipolar, and multipolar systems. Thus, implantable leads with or without ring electrodes are equally contemplated without departing from the scope of the invention.

Furthermore, even though only one lead 4 for implantation and stimulation in the right ventricle is illustrated in the drawing, the medical implant 2 may be connected to further leads, for instance for sensing and or stimulation of the right atrium, the left atrium, and/or the left ventricle. The leads may comprise sensors for sensing and conducting electrical signals from the heart, and/or sensors for sensing other physiological parameters, such as pressures, temperatures, etc. within the heart. A single electrode or sensor may further be used for multiple purposes, such as delivering electrical stimuli and sensing electrical signals, or sensing electrical signals and pressures, etc.

For the purposes of the presently illustrated embodiments, the ring electrode 7 and/or the tip electrode 10 may constitute the temperature sensitive element connectable to a device for monitoring the status of an implantable lead in accordance with the present invention. However, other positions on the implantable lead and configurations of the temperature sensitive element are also contemplated without departing from the scope of the present invention.

Figure 2:
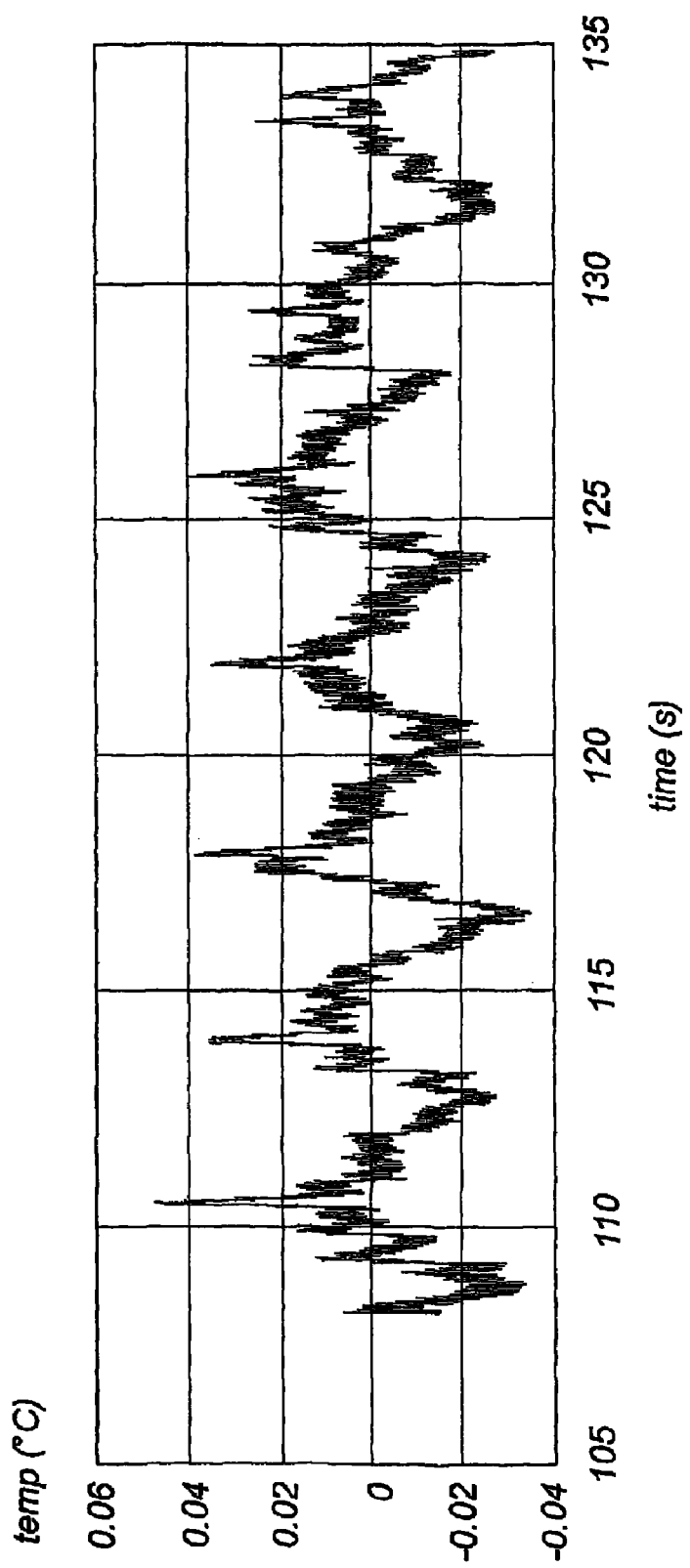
FIG. 2 is a diagram illustrating intracardiac blood temperature variations

With reference now to FIG. 2, there is shown a diagram illustrating temperature variations in the intraventricular blood stream of a human patient during ventilation. The diagram illustrates both the larger long-term variations occurring within a respiratory cycle, which for the purposes of the illustrated measurements is about 4 seconds, and the smaller short-term variations occurring within a heart beat cycle. The latter can be seen as a ripple on the blood temperature curve. In the illustrated measurements, the long-term variations during a single respiratory cycle, or a single breath, is in the range of 0.03-0.05° C., and the short-term variations during a single heart beat cycle is in the range of 0.005-0.02° C.

Figure 3:
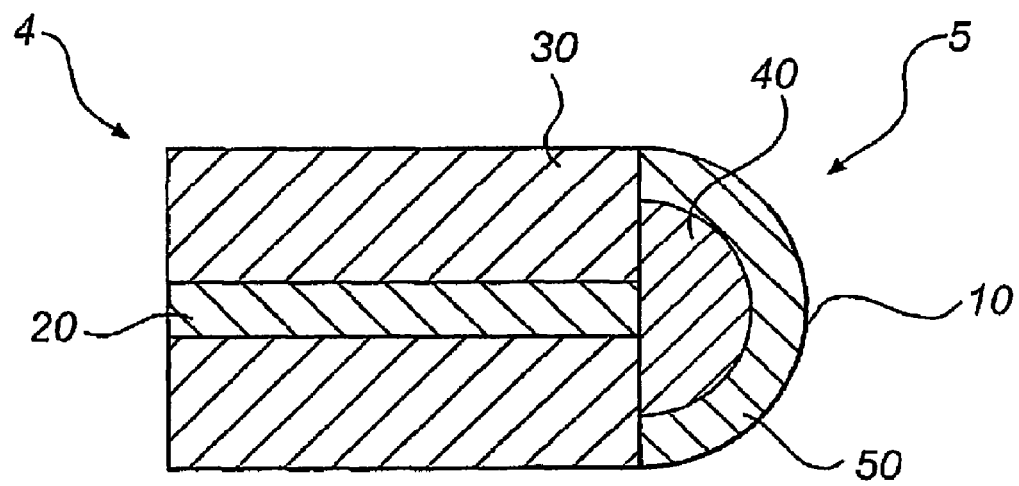
FIGS. 3 and 4 are schematic drawings of two embodiments of a tip electrode including a temperature sensitive element.
Figure 4:
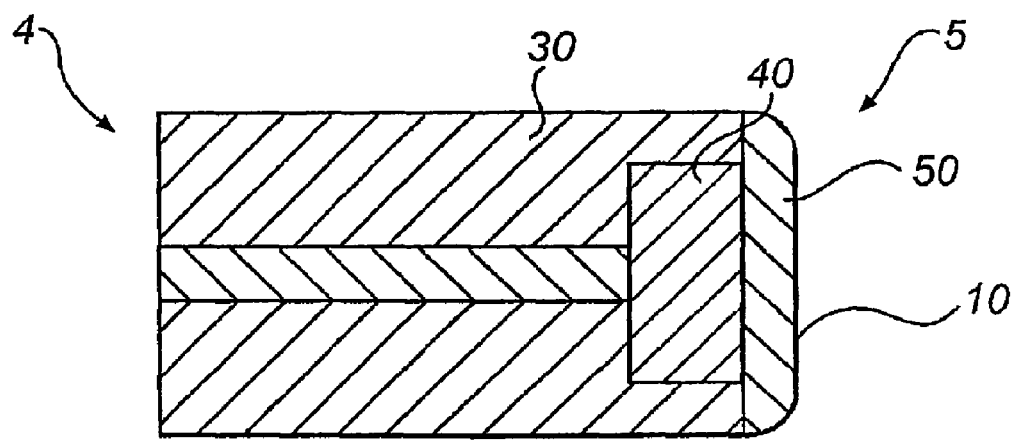

With reference now to FIGS. 3 and 4, there is shown the distal end 5 of an implantable lead 4 for a heart pacemaker, and in particular a tip electrode 10 constituting both a stimulating electrode and a temperature sensitive element. The electrode 10 comprises a conductor 20 enclosed by an insulator 30, e.g. made from silicon rubber. The conductor 20 is at one end in contact with an electrically conductive core 40, which is covered with a piezoelectric material 50, preferably formed of $Na_{0.5}K_{0.5}NbO_3$. In order to obtain a high capacitance, usually of the order 10-100 nF, the layer of piezoelectric material is very thin (0.1-5 pm). The conductive core 40 and the piezoelectric layer 50, i.e. the piezoelectric electrode, form the tip of the implantable lead 4.

FIGS. 3 and 4 show a hemispherical and a planar embodiment of the tip, respectively, wherein the planar embodiment is more sensitive to how it is placed with respect to the myocardial tissue. In one embodiment, the conductor 20 is made of the commonly used alloy MP35 and the conductive core 40 is made of e.g. graphite, titanium, platinum, or iridium. The size of the electrode is about the same as for standard cardiac stimulator electrodes and may for instance vary between 1-10 $mm^2$.

Thus, the stimulating or tip electrode 10 is not only arranged to deliver electrical stimuli to the heart, but is also arranged as a temperature sensitive element capable of providing an output signal indicative of temperature variations occurring in the biological matter in contact with the sensor or electrode surface.

Figure 5:
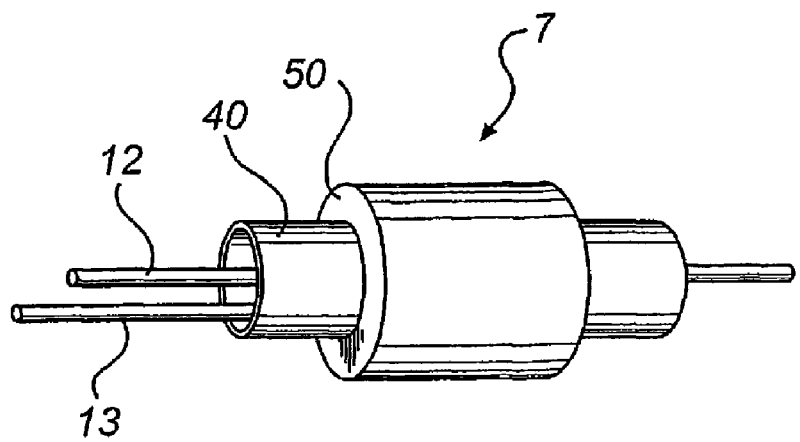
FIGS. 5 and 6 are schematic drawings of embodiments of a ring electrode including a temperature sensitive element.
Figure 6:
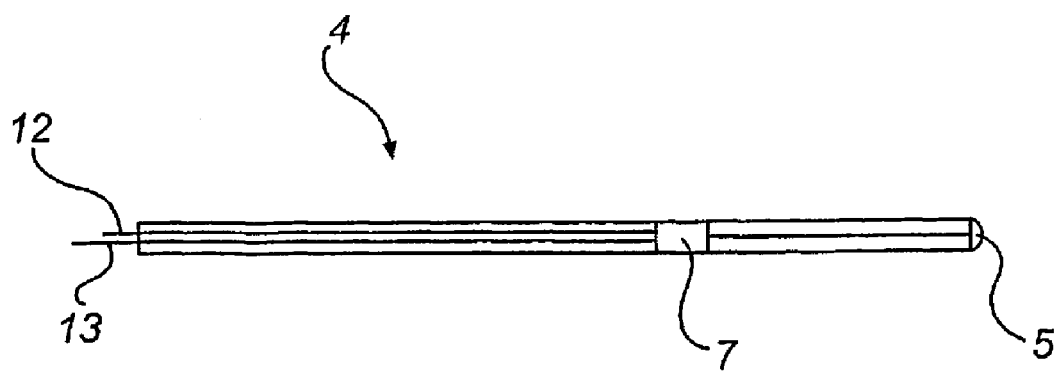

According to another embodiment of an implantable lead comprising a temperature sensitive element, FIGS. 5 and 6 show an annular or coaxial piezoelectric sensor or electrode 7 constituting a temperature sensitive element. The annular electrode 7 may be positioned from about 3 mm to 15 cm proximally of the distal end or tip 5, and is intended to be positioned in the intracardiac blood stream when the lead is in the implanted state. This embodiment may e.g. be used in a single lead DDD pacemaker system as disclosed in U.S. Pat. No. 5,476,499.

In the same manner as described above in relation to FIGS. 3 and 4, the electrode 7 comprises a conductor 13 enclosed by an insulator (not shown), e.g. silicon rubber. The conductor 13 is at one end in contact with an electrically conductive core 40, which is covered with a piezoelectric material 50, preferably formed of $Na_0.5K_{0.5}NbO_3$. In this embodiment, the lead further comprises a second conductor 12 connected to the temperature sensitive element for enabling an AC vibration exciting current to be applied.

In operation, the temperature sensitive elements are connected to the heart stimulator 2 for delivering an output signal, or temperature signal, indicative of temperature changes to which the element has been subjected. Electric circuits for measuring such an output signal from the temperature sensitive element are not further described herein since it is well-known to a person skilled in the art how such circuits can be designed.

The stimulator includes processing circuitry (not shown) for monitoring the status of the implantable lead on the basis of said output signal. The interpretation of the output signal is dependent on several factors, such as the positioning of the sensor on the implantable lead, the intended positioning within the heart, the desired status information, etc.

As an example, if the temperature sensitive element is arranged at the very tip of the implantable lead, e.g. arranged at or as the stimulating electrode, then the desired status information would be whether the distal end becomes dislocated from an ingrown or embedded position. Thus, it would be desirable to detect a sudden or slow but significant increase in temperature variations which could indicate that dislocation has occurred.

As a further example, if the temperature sensitive element is arranged at a location on the implantable lead which is intended to be located in the blood stream, e.g. at or as a sensor for measuring parameters of the blood, then a desired status information could be to detect whether the element has come into contact with the ventricular or atrial wall, or whether the element is subjected to overgrowth. Both of these status changes could possibly have an impairing effect on the sensing ability of the sensor.

According to specific embodiments, the temperature sensitive element could be arranged to have self-cleaning properties. In these embodiments, the element is made from a piezoelectric material which is caused to vibrate upon applying an AC vibrating voltage across the element. This can for instance be performed periodically in order to prevent detrimental build-up of adhering substances to the surface of the element. In another example, the vibrating voltage for removing adhering and clotting substances could be applied following the determination of suspected tissue overgrowth, i.e. when the output signal of the temperature sensitive element indicates a decrease or changed morphology in the temperature variations experienced by the element within a respiratory cycle or a heart beat cycle.

Although modifications and changes may be suggested by those skilled in the art, it is the intention of the inventors to embody within the patent warranted heron all changes and modifications as reasonably and properly come within the scope of their contribution to the art.

We claim as our invention:

1. A cardiac lead monitoring device comprising:
   a cardiac lead configured for implantation in a human heart;
   a temperature sensitive element carried by said cardiac lead, said temperature sensitive element having a surface configured for contact with biological matter and emitting a temperature signal after implantation of said cardiac lead representing temperature variation of said biological matter in contact with said surface; and
   processing circuitry configured to receive said temperature signal and to determine, also after implantation of said cardiac lead, a temperature signal variability in said temperature signal within a selected time interval, said temperature signal variability representing variability of said temperature of said biological matter within said selected time interval, and to compare said temperature signal variability with a threshold value related to temperature changes occurring in blood within the heart during said selected time interval, to obtain a comparison result and to emit a status signal indicative of a status of the cardiac lead after implantation dependent on said comparison, wherein said processing circuit is configured to emit said status signal as indicative of an extent of ingrowth of at least a portion of said cardiac lead into myocardial tissue.

2. A device as claimed in claim 1 wherein said processing circuitry is configured to monitor progression of said ingrowth following implantation by comparing respective status signals obtained at successive points in time.

3. A cardiac lead monitoring device comprising:
   a cardiac lead configured for implantation in a human heart;
   a temperature sensitive element carried by said cardiac lead, said temperature sensitive element having a surface configured for contact with biological matter and emitting a temperature signal after implantation of said cardiac lead representing temperature variation of said biological matter in contact with said surface; and
   processing circuitry configured to receive said temperature signal and to determine, also after implantation of said cardiac lead, a temperature signal variability in said temperature signal within a selected time interval, said temperature signal variability representing variability of said temperature of said biological matter within said selected time interval, and to compare said temperature signal variability with a threshold value related to temperature changes occurring in blood within the heart during said selected time interval, to obtain a comparison result and to emit a status signal indicative of a status of the cardiac lead after implantation dependent on said comparison, wherein said processing circuitry is configured to emit said status signal as indicative of an extent to which said temperature sensitive element exhibits tissue overgrowth and protein adherence.

4. A cardiac lead monitoring device comprising:
   a cardiac lead configured for implantation in a human heart;
   a temperature sensitive element carried by said cardiac lead, said temperature sensitive element having a surface configured for contact with biological matter and emitting a temperature signal after implantation of said cardiac lead representing temperature variation of said biological matter in contact with said surface; and
   processing circuitry configured to receive said temperature signal and to determine, also after implantation of said cardiac lead, a temperature signal variability in said temperature signal within a selected time interval, said temperature signal variability representing variability of said temperature of said biological matter within said selected time interval, and to compare said temperature signal variability with a threshold value related to temperature changes occurring in blood within the heart during said selected time interval, to obtain a comparison result and to emit a status signal indicative of a status of the cardiac lead after implantation dependent on said comparison, wherein said processing circuitry is configured to employ a heartbeat cycle of the heart as said selected time interval.

5. A device as claimed in claim 4 wherein said processing circuitry is configured to emit said status signal as an indicator of an extent to which said surface of said temperature sensitive element is in contact with blood.

6. A device as claimed in claim 4 wherein said processing circuitry is configured to emit said status signal as indicative of whether said cardiac lead is at least partly dislocated from an implanted position.

7. A device as claimed in claim 6 wherein said processing circuitry is configured to emit said status signal as indicative of at least partial dislocation of a distal end portion of said cardiac lead that has ingrown into myocardial tissue.

8. A device as claimed in claim 7 wherein said processing circuitry is configured to emit said status signal upon a rapid and substantial increase in said temperature signal variability.

9. A cardiac lead monitoring device comprising:
    a cardiac lead configured for implantation in a human heart;
    a temperature sensitive element carried by said cardiac lead, said temperature sensitive element having a surface configured for contact with biological matter and emitting a temperature signal after implantation of said cardiac lead representing temperature variation of said biological matter in contact with said surface; and
    processing circuitry configured to receive said temperature signal and to determine, also after implantation of said cardiac lead, a temperature signal variability in said temperature signal within a selected time interval, said temperature signal variability representing variability of said temperature of said biological matter within said selected time interval, and to compare said temperature signal variability with a threshold value related to temperature changes occurring in blood within the heart during said selected time interval, to obtain a comparison result and to emit a status signal indicative of a status of the cardiac lead after implantation dependent on said comparison, wherein said processing circuitry is configured to employ a respiration cycle as said selected time interval.

10. An implantable cardiac stimulator comprising:
    a housing configured for implantation in a subject;
    a pulse generator contained in said housing that generates stimulation pulses;
    control circuit connected to said pulse generator that controls emission of said stimulation pulses by said pulse generator;
    a cardiac lead connected to said pulse generator and configured for implantation in the subject, said cardiac lead being configured to conduct said stimulation pulses to the heart;
    processing circuitry contained in said housing;
    a temperature sensitive element carried by said cardiac lead, said temperature sensitive element having a surface configured for contact with biological matter and emitting a temperature signal after implantation of said cardiac lead indicative of temperature variation of the biological matter in contact with said surface, said cardiac lead having a conductor that conducts said temperature signal from said temperature sensitive element to said processing circuitry; and
    said processing circuitry being configured to determine, also after implantation of said cardiac lead, a temperature signal variability in said temperature signal within a selected time interval, said temperature signal variability being indicative variability in said temperature of said biological matter within said selected time interval, and to compare said temperature signal variability with a threshold value related to temperature changes occurring in blood within the heart during said selected time interval, to obtain a comparison result, and to emit a status signal indicative of a status of the cardiac lead after implantation dependent on said comparison result;
    wherein said processing circuitry is configured to emit said status signal as indicative of said temperature sensitive element having excessive tissue overgrowth and protein adherence, and wherein said processing circuitry is connected to said voltage source to cause said voltage source to apply said vibration-exciting voltage in response to said status signal.

11. An implantable cardiac stimulator as claimed in claim 10 wherein said temperature sensitive element is comprised of piezoelectric material, and wherein said implantable cardiac stimulator comprises a voltage source connected to said temperature sensitive element via said cardiac lead that applies a vibration-exciting voltage to said temperature sensitive element.

12. An implantable cardiac stimulator as claimed in claim 10 wherein said temperature sensitive element has an annular shape around a circumference of said cardiac lead.

13. A method for monitoring a status of a cardiac lead implanted in a human heart, comprising the steps of:
    implanting a cardiac lead, carrying a temperature sensitive element, in a human heart to place a surface of said temperature sensitive element in contact with biological matter;
    after implantation of said cardiac lead, emitting a temperature signal from said temperature sensitive element indicative of a temperature of said biological matter in contact with said surface of said temperature sensitive element;
    also, after implantation of said cardiac lead, automatically electronically determining a temperature signal variability in said temperature signal within a selected time interval, said temperature signal variability being indicative of a variability of the temperature of said biological matter within said selected time interval;
    automatically electronically comparing said temperature signal variability with a threshold value related to temperature changes occurring in blood within the heart during said selected time interval, to obtain a comparison result;
    generating a status signal indicative of a status of said implantable lead after implantation dependent on said comparison result; and
    generating said status signal as indicative of an extent of ingrowth of a distal end portion of said cardiac lead into myocardial tissue.

14. A method as claimed in claim 13 comprising monitoring progression of said ingrowth after implantation by comparing respective status signal obtained at successive points in time.

15. A method for monitoring a status of a cardiac lead implanted in a human heart, comprising the steps of:
    implanting a cardiac lead, carrying a temperature sensitive element, in a human heart to place a surface of said temperature sensitive element in contact with biological matter;
    after implantation of said cardiac lead, emitting a temperature signal from said temperature sensitive element indicative of a temperature of said biological matter in contact with said surface of said temperature sensitive element;
    also, after implantation of said cardiac lead, automatically electronically determining a temperature signal variability in said temperature signal within a selected time interval, said temperature signal variability being indicative of a variability of the temperature of said biological matter within said selected time interval;

automatically electronically comparing said temperature signal variability with a threshold value related to temperature changes occurring in blood within the heart during said selected time interval, to obtain a comparison result;

generating a status signal indicative of a status of said implantable lead after implantation dependent on said comparison result; and generating said status signal as an indicator of an extent to which said temperature sensitive element exhibits excessive tissue overgrowth and protein adherence.

16. A method for monitoring a status of a cardiac lead implanted in a human heart, comprising the steps of:

implanting a cardiac lead, carrying a temperature sensitive element, in a human heart to place a surface of said temperature sensitive element in contact with biological matter;

after implantation of said cardiac lead, emitting a temperature signal from said temperature sensitive element indicative of a temperature of said biological matter in contact with said surface of said temperature sensitive element;

also, after implantation of said cardiac lead, automatically electronically determining a temperature signal variability in said temperature signal within a selected time interval, said temperature signal variability being indicative of a variability of the temperature of said biological matter within said selected time interval;

automatically electronically comparing said temperature signal variability with a threshold value related to temperature changes occurring in blood within the heart during said selected time interval, to obtain a comparison result;

generating a status signal indicative of a status of said implantable lead after implantation dependent on said comparison result; and employing a heartbeat cycle of the subject as said selected time interval.

17. A method for monitoring a status of a cardiac lead implanted in a human heart, comprising the steps of:

implanting a cardiac lead, carrying a temperature sensitive element, in a human heart to place a surface of said temperature sensitive element in contact with biological matter;

after implantation of said cardiac lead, emitting a temperature signal from said temperature sensitive element indicative of a temperature of said biological matter in contact with said surface of said temperature sensitive element;

also, after implantation of said cardiac lead, automatically electronically determining a temperature signal variability in said temperature signal within a selected time interval, said temperature signal variability being indicative of a variability of the temperature of said biological matter within said selected time interval;

automatically electronically comparing said temperature signal variability with a threshold value related to temperature changes occurring in blood within the heart during said selected time interval, to obtain a comparison result;

generating a status signal indicative of a status of said implantable lead after implantation dependent on said comparison result; and employing a respiration cycle of the subject as said selected time interval.

18. A method as claimed in claim 17 comprising generating said status signal as an indicator of an extent to which said surface of said temperature sensitive element is in contact with blood.

19. A method as claimed in claim 17 comprising generating said status signal as an indicator of whether said implantable lead is at least partially dislocated from an implanted position.

20. A method as claimed in claim 17 comprising generating said status signal as indicative of a partial dislocation of a distal end portion of said cardiac lead that has been ingrown with myocardial tissue.

21. A method as claimed in claim 20 comprising generating said status signal upon a rapid and substantial increase in said temperature signal variability.

22. A method as claimed in claim 17 wherein said temperature sensitive element is comprised of a piezoelectric material, and comprising applying a vibration-exciting voltage to said temperature sensitive element that cleans said surface of said temperature sensitive element from tissue overgrowth and protein adherence.

23. A method as claimed in claim 22 comprising generating said status signal as an indicator of said excessive tissue overgrowth and protein adherence, and applying said vibration exciting voltage dependent on said status signal.

* * * * *